United States Patent [19]

Simon et al.

[11] Patent Number: 4,560,548
[45] Date of Patent: Dec. 24, 1985

[54] BONE SEEKING TC-99M COMPLEXES OF PHOSPHONATE DERIVATIVES OF BIS(AMINOALKYL)PIPERAZINE

[75] Inventors: Jaime Simon, Angleton; David A. Wilson, Richwood, both of Tex.; Wynn A. Volkert, Columbia, Mo.; Druce K. Crump, Lake Jackson, Tex.

[73] Assignee: The Dow Chemical Company, Midland, Mich.

[21] Appl. No.: 598,633

[22] Filed: Apr. 10, 1984

[51] Int. Cl.[4] .................... A61K 49/00; A61K 43/00
[52] U.S. Cl. ........................................ 424/1.1; 424/9; 260/502.4 P; 260/502.5 R
[58] Field of Search ................... 424/1.1, 9; 260/502.4 P, 502.5 R

[56] References Cited

U.S. PATENT DOCUMENTS

| | | | |
|---|---|---|---|
| 3,851,044 | 11/1974 | Adler et al. | 423/249 |
| 3,852,414 | 12/1974 | Adler et al. | 424/1.1 |
| 3,931,396 | 1/1976 | Bardy et al. | 424/1.1 |
| 3,983,227 | 9/1976 | Tofe et al. | 424/1.1 |
| 3,989,730 | 11/1976 | Subramanian et al. | 260/429.7 |
| 4,016,249 | 4/1977 | Adler et al. | 424/1.1 |
| 4,032,625 | 6/1977 | Subramanian et al. | 424/1.1 |
| 4,075,314 | 2/1978 | Wolfangel et al. | 424/1.1 |
| 4,082,840 | 4/1978 | Adler et al. | 424/1.1 |
| 4,187,284 | 2/1980 | Rolleston et al. | 424/1.1 |
| 4,234,562 | 11/1980 | Tofe et al. | 424/1.1 |
| 4,385,046 | 5/1983 | Milbrath et al. | 424/1.1 |
| 4,387,087 | 6/1983 | Deutsch et al. | 424/1.1 |

FOREIGN PATENT DOCUMENTS

| | | | |
|---|---|---|---|
| 1518118 | 12/1973 | Fed. Rep. of Germany | 424/1.1 |
| 1081124 | 8/1967 | United Kingdom | 424/1.1 |

OTHER PUBLICATIONS

Nishiyama, J. Null. Med., 23 (1982) 1102–1110.
Deutsch et al., J. Null. Med., 22 (1981) 897–907.
Radiology, vol. 99, pp. 192–196, 1971.
Radiology, 136:209–211, Jul. 1980.
Radiology, 136: pp. 747–751, Sep. 1980.
J. Nuc. Med. 21: pp. 767–770 (1980).
J. Nuc. Med. 21, pp. 961–966 (1980).

Primary Examiner—Christine M. Nucker
Attorney, Agent, or Firm—A. C. Ancona

[57] ABSTRACT

Radionuclide complexes of phosphonate derivatives of bis(aminoalkyl)piperazine have been found which are useful for imaging and/or treating therapeutically the skeletal system to detect and treat bone tumors. These complexes clear readily through the kidneys and the ratio of uptake in bone to that in surrounding soft tissue is high.

20 Claims, No Drawings

BONE SEEKING TC-99M COMPLEXES OF PHOSPHONATE DERIVATIVES OF BIS(AMINOALKYL)PIPERAZINE

BACKGROUND OF THE INVENTION

The first radionuclide to be widely used for bone scanning was Sr-85. Strontium-85 is rapidly accumulated by bone after intravenous administration and images of the skeletal system are possible. However, Sr-85 has a long physical half life (65 days) and a long biological half life (~800 days) which limits the levels which can be administered. Also, the high energy of the gamma photon emitted (514 kev) is difficult to collimate.

Fluorine-18 has also been used to image the skeletal system. It is a positron emitter with a half life of 1.85 hr. Although F-18 has good physical properties for imaging, it has some serious drawbacks. Fluorine-18 is cyclotron produced and, therefore, expensive. Also its distribution is limited due to its short half life.

Many organ scanning agents, including those for the skeletal system, have now been replaced with complexes of Technetium-99m. This nuclide has ideal physical properties ($T_{\frac{1}{2}}=6$ hr., gamma photon of 141 kev) for imaging. In addition, it is readily available because of the Mo-99/Tc-99m generators. Thus, the majority of imaging is now done using Tc-99m.

Technetium-99m is obtained from generators in the +7 oxidation state as the pertechnetate ion ($TcO_4^-$). In order to form a complex, Tc must be in a lower oxidation state, i.e. +3, +4 or +5. Although other reducing agents can be used, $Sn^{2+}$ has been employed most often. Thus Tc-99m complexes can be formed by reduction of $TcO_4^-$ using $Sn^{2+}$ in the presence of a complexing agent. This is usually done in an aqueous saline solution that is suitable for intravenous injection.

Commercial complexing agents are sold as "radiopharmaceutical kits". A "kit" consists of an evacuated vial containing the complexing agent, a reducing agent, and possibly a buffer and stabilizers. To prepare the Tc-99m complexes, a few milliliters of sodium pertechnetate solution in saline is injected into the vial. An adequate amount of the resultant solution is used for imaging.

Subramanian et al (Radiology, Vol. 99, pp. 192–196, 1971) reported the use of a complex of Tc-99m and an inorganic polyphosphate for skeletal imaging. Several others have reported inorganic polyphosphates as useful for this purpose (see U.S. Pat. Nos. 3,852,414; 4,016,249; and 4,082,840). The use of pyrophosphate (PYP) for bone imaging has also been taught (U.S. Pat. Nos. 3,851,044; 3,931,396; and 4,075,314). The Tc-phosphates had fair success but have been replaced by Tc-phosphonates.

Complexes of Tc-99m with phosphonic acids show higher bone uptake with faster blood clearance than Tc-99m/phosphate complexes. Phosphonic acids which are considered the best bone scanning agents when complexed with Tc-99m include hydroxyethanediphosphonate (EHDP), methylenediphosphonate (MDP) and hydroxymethylenediphosphonate (see U.S. Pat. Nos. 3,983,227; 3,989,730; 4,032,625 and also J. Nucl. Med. 21, pg. 767; Radiology 136, pg. 209; J. Nucl. Med. 21, pg. 961; Radiology 136, pg. 747).

Another application for skeletal agents is as a therapeutic agent. It may be possible to treat skeletal tumors with a particle emitting e.g. beta, radionuclide if it can be concentrated in the area of the tumor. Therefore, if a particle-emitting agent that had a high uptake in the tumor and relatively low uptake in normal bone was found, it could prove to be an effective therapeutic agent. (See Weinenger, J., Ketriing, A. R., et al J. Nucl. Med. 24, p. 23, 1983)

Several nuclides may be of therapeutic utility. For example Re-186 has a half life of 90.6 hr. and beta-radiation of 1.076 and 0.939 MeV. Also, since the chemistry of Re is very similar to that of Tc, it is probable that the biolocalization of Re-complexes would be similar to that of Tc-complexes. There are other nuclides, especially of the lanthanide group of metals, that may also be therapeutically useful.

SUMMARY OF THE INVENTION

New stable complexing agents for radionuclides which are phosphonate derivatives of certain bis(aminoalkyl)piperazines have been found which are useful in imaging the skeletal system in animals. The complexes readily clear through the kidneys with large amounts being taken up in the bone. The ratio of uptake in bone to that in surrounding soft tissue is high.

DETAILED DESCRIPTION OF THE INVENTION

This invention concerns the use of novel complexes for imaging the skeletal system and for possible treatment of skeletal metastasis. The complexing agents were found to form stable Tc-99m complexes when $Sn^{2+}$ was added to a saline solution containing the complexing agent. The complexes cleared readily through the kidneys with a large amount being taken up by the skeletal system.

The complexed radioactive agents concentrate in bone and yield bone scans of diagnostic quality. Specifically, Tc-99m complexes with chelates from piperazine and piperazine analogues. The chelating agents are prepared by reacting piperazine derivatives with formaldehyde and phosphorous acid. The complexing agent is mixed with Tc-99m in the form of $TcO_4^-$ and a reducing agent to form the chelate. Scintillation scans of rats injected with the said chelates compared favorably to those using commercial bone scanning agents.

The description of the preparation of the chelating compounds is disclosed in our copending application Ser. No. 583,526 filed Feb. 24, 1984 entitled "Bis(aminoalkyl)Piperazine Derivatives and Their Use as Metal Ion Control Agents."

The chelating compounds which form the Tc-99m complexes useful in the process of the present invention have the formula

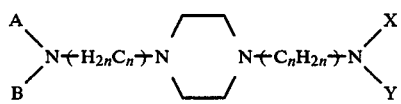

wherein n is 2 or 3 and wherein substituents A, B, X and Y each are independently selected from radicals consisting of hydrogen, hydroxyalkyl (wherein the alkyl group contains 2–6 carbon atoms), methylenephosphonic, methylene-, ethylene- and propylenesulfonic, hydroxymethyl-, hydroxyethyl- and hydroxypropylsulfonic acid radicals, carboxylic acid radicals (having 2–4 carbon atoms) and the alkali or alkaline earth metal, ammonia and amine salts of any of the phosphonic, sulfonic or carboxylic acid derivatives. At least one of A, B, X and Y substituents must be a methylenephosphonic acid or salt thereof.

Representative of the preparation is the following description.

CHELATE PREPARATION

Example 1

Deionized water (100 g) and 25.65 g, 0.15 moles of N,N'-bis(aminoethyl)piperazine were weighed into a 500-ml round-bottom flask equipped with a water-cooled reflux condenser, heating mantle, mechanical stirrer, thermometer, temperature controller, and an addition funnel. Approximately 74.5 g of concentrated HCl and 73.8 g, 0.63 mole of 70% $H_3PO_3$, 15 g $H_2O$ were added. The reaction mixture was heated to reflux for 30 minutes. Aqueous 37% formaldehyde (50.75 g) was added dropwise while heating and stirring over a period of one hour. The solution was refluxed for an additional 1.5 hours. The precipitated product was recovered by filtration and dried. The compound was the tetramethylenephosphonic acid derivative of N,N'-bis-(aminoethyl)piperazine.

PREPARATION OF THE RADIOACTIVE COMPLEX

Example 2

Fifty mg of the chelate of Example 1 was added to a vial containing 2 ml of 0.9% NaCl solution. The pH was adjusted to 3-5 using dilute NaOH and HCl. To this solution, 0.1 ml of freshly eluted $^{99m}TcO_4^-$ solution was added, followed by the addition of 100 µl of a freshly prepared saturated stannous tartrate solution. Paper chromatography strips eluted with saline or acetone yielded less than 5% $TcO_4^-$ or reduced uncomplexed $^{99m}Tc$.

UTILIZATION OF THE RADIOACTIVE CHELATE

Example 3

Fifty microliters (~1/mCi) of the complex of Example 2 was injected into the tail vein of anesthesized rats. Scintillation scans of the rats several times post injection were obtained. These compared favorably with those done with commercially available bone scanning agents.

Example 4

In a manner similar to Example 1, N,N'-bis(aminopropyl)piperazine was reacted with formaldehyde and phosphorus acid to obtain the tetramethylenephosphonic acid derivative.

This product was in turn reacted as in Example 2 to obtain the radioactive complex of $^{99m}TcO_4^-$ with the methylenephosphonic acid compound.

Fifty microliters (~1/mCi) of the said complex was injected into the tail veins of laboratory rats. After 120 minutes, the rats were killed and samples of several tissues and organs taken. These were weighed and the activity measured using a NaI counter.

The percent of the dose injected found in the skeleton and urine was 32% and 63%, respectively. Low amounts of activity were found in soft tissue (e.g. liver 0.06, muscle 0.02% dose/g × 1% body wt.). The ratio of activity found in bone to muscle was 208. The same ratio for a commercial bone agent (Tc-MDP) was found to be 150.

We claim:

1. A bone seeking complex of a radioactive nuclide and a compound having the structural formula

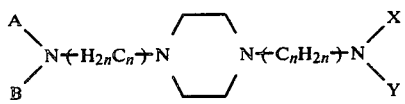

wherein n is 2 or 3 and wherein substituents A, B, X and Y each are independently selected from radicals consisting of hydrogen, hydroxyalkyl (wherein the alkyl group contains 2-6 carbon atoms), methylenephosphonic, methylene-, ethylene- and propylenesulfonic, hydroxymethyl-, hydroxyethyl- and hydroxypropylsulfonic acid radicals, carboxylic acid radicals (having 2-4 carbon atoms) and the alkali or alkaline earth metal, ammonium and amine salts of any of said phosphonic, sulfonic or carboxylic acid derivatives and wherein at least one of A, B, X and Y is a methylenephosphonic acid radical or salt thereof.

2. The complex of claim 1 wherein each of A, B, X and Y are methylenephosphonic acid radicals or salts thereof.

3. The complex of claim 1 wherein the radioactive nuclide is Technetium-99m.

4. The complex of claim 2 wherein the radioactive nuclide is Technetium-99m.

5. A composition comprising the complex of claim 3 and a reducing agent in a saline solution.

6. A composition comprising the complex of claim 4 and a reducing agent in a saline solution.

7. The composition of claim 5 wherein the reducing agent is $Sn^{2+}$.

8. The composition of claim 6 wherein the reducing agent is $Sn^{2+}$.

9. The composition of claim 1 wherein the radioactive nuclide is a particle emitter.

10. The composition of claim 2 wherein the radioactive nuclide is a particle emitter.

11. The composition of claim 9 wherein the radionuclide is Re-186.

12. The composition of claim 10 wherein the radionuclide is Re-186.

13. A composition comprising the complex of claim 11 and a reducing agent in a saline solution.

14. A composition comprising the complex of claim 12 and a reducing agent in a saline solution.

15. The composition of claim 13 wherein $Sn^{2+}$ is the reducing agent.

16. The composition of claim 14 wherein $Sn^{2+}$ is the reducing agent.

17. The composition of claim 9 wherein the radionuclide is one of the lanthanide series of the periodic table.

18. The composition of claim 10 wherein the radionuclide is one of the lanthanide series of the periodic table.

19. In a process in which the skeletal system is imaged with a complex of a radionuclide the improvement which comprises employing as the complexing agent a compound having the formula

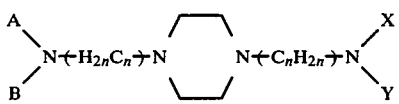

wherein n is 2 or 3 and wherein substituents A, B, X and Y each are independently selected from radicals consisting of hydrogen, hydroxyalkyl (wherein the alkyl group contains 2-6 carbon atoms), methylenephosphonic, methylene-, ethylene- and propylenesulfonic, hydroxymethyl-, hydroxyethyl- and hydroxypropylsulfonic acid radicals, carboxylic acid radicals (having 2-4 carbon atoms) and the alkali or alkaline earth metal, ammonium and amine salts of any of the phosphonic, sulfonic or carboxylic acid derivatives and wherein at least one of A, B, X and Y is a methylenephosphonic acid radical or salt thereof.

20. The process of claim 19 wherein each of A, B, X and Y is a methylenephosphonic acid radical or a salt thereof.

* * * * *